United States Patent
Cain

(10) Patent No.: US 6,281,406 B1
(45) Date of Patent: Aug. 28, 2001

(54) ADSORPTION PROCESS FOR PARAXYLENE PURIFACATION USING CS SSZ-25 ADSORBENT WITH BENZENE DESORBENT

(75) Inventor: John J. Cain, Berkeley, CA (US)

(73) Assignee: Chevron Corporation, San Francisco, CA (US)

(*) Notice: Subject to any disclaimer, the term of this patent is extended or adjusted under 35 U.S.C. 154(b) by 0 days.

(21) Appl. No.: 09/540,912

(22) Filed: Mar. 31, 2000

(51) Int. Cl.[7] .................................................. C07C 7/12
(52) U.S. Cl. ......................... 585/820; 585/828; 585/831
(58) Field of Search ................... 585/820, 828, 585/831

(56) References Cited

U.S. PATENT DOCUMENTS

| | | | |
|---|---|---|---|
| 3,868,429 | * 2/1975 | Faulkner | 585/820 |
| 4,054,388 | * 10/1977 | Bailey | 208/89 |
| 4,439,409 | 3/1984 | Puppe et al. | 423/328 |
| 4,826,667 | 5/1989 | Zones et al. | 423/277 |
| 4,954,325 | 9/1990 | Rubin et al. | 423/328 |

* cited by examiner

*Primary Examiner*—Walter D. Griffin
*Assistant Examiner*—Tam M. Nguyen
(74) *Attorney, Agent, or Firm*—David M. Tuck; Charles W. Stewart

(57) ABSTRACT

An adsorption process for the recovery of paraxylene from mixed xylenes using a molecular sieve adsorbent comprising SSZ-25, MCM-22, PSH-3, ERB-1, or ITQ-1. A preferred desorbent for the process is benzene. A hybrid adsorption/crystallization PX purification process is also described using the molecular sieve adsorbent.

17 Claims, No Drawings

ADSORPTION PROCESS FOR PARAXYLENE PURIFACATION USING CS SSZ-25 ADSORBENT WITH BENZENE DESORBENT

FIELD OF THE INVENTION

This invention relates to the separation of xylene isomers and ethylbenzene comprising the use of an adsorption process for paraxylene recovery and purification, to produce high purity paraxylene.

BACKGROUND OF THE INVENTION

Paraxylene is a valuable petrochemical precursor for the production of terephthalate polymers such as polyethylene terephthalate. Polyethylene terephthalate is the polymer in several large scale end uses including polyester fibers and PET bottle resin. The large market for paraxylene for fiber and PET resin creates a need for large scale production and purification facilities for paraxylene. Paraxylene (PX) is typically isolated in refineries from the reformate produced by catalytic reformers although it can come other sources such as pygas. Catalytic reformers produce xylene molecules by the dehydrocyclization of straight and branched chain paraffins, the dehydrogenation of naphthenes, and to a small extent the dealkylation of polyalkylaromatics. The $C_8$ aromatic portion of the reformate contains more than just paraxylene. The other aromatic isomers present in $C_8$ boiling range reformate are orthoxylene (OX), metaxylene (MX), and ethylbenzene (EB). These isomers are difficult or impossible to separate from the paraxylene by distillation because they have close boiling points.

Two methods that have been developed to isolate the paraxylene (PX) from the other $C_8$ isomers are crystallization and adsorption. Continuous simulated moving bed adsorption is currently used in most grass roots PX separation plants. Examples of such PX adsorption processes include Parex (UOP) and Eluxyl (IFP). These processes utilize an X or Y zeolite adsorbent in combination with either toluene or para-diethylbenzene as a desorbent. Selection of a desorbent is an important consideration and has significant impact on the design and economics of the process. In general the desorbent should be adsorbed about as well as the feed components on the selected adsorbent. If the desorbent is adsorbed too tightly to the adsorbent, an excessive fraction of the total capacity of the adsorbent is occupied by the desorbent. This effectively reduces the portion of the adsorbent that is available to adsorb and separate the $C_8$ aromatic isomers, and increases the amount of adsorbent that must be used. If the desorbent is not adsorbed tightly enough large amounts of desorbent must be used causing a high desorbent to feed ratio. A high ratio of desorbent to feed results in the need for larger extract and raffinate distillation columns. The extract column separates the PX product from the desorbent. In a PX process the raffinate column separates the desorbent from the other $C_8$ aromatic isomers. These distillation columns are a major part of the expense of a PX separation process. They are both a large portion of the capital cost of the process and cause a large portion of the operating cost of the PX separation plant. Thus it is generally best to minimize the amount of desorbent used in the process. Another important parameter of the desorbent is its boiling point. Since the desorbent is separated from the raffinate and the extract by distillation it is desirable to select a desorbent with a boiling point that is substantially different from the extract and raffinate boiling ranges. The closer the desorbent boiling point to the PX extract or $C_8$ aromatic raffinate boiling range, the larger the column required and the higher the utility costs to operate the column. Also it is important to select a desorbent that does not form an azeotrope with any of the feed components in order to have a clean separation.

As discussed above adsorbents used for commercial PX separation from mixed xylenes typically comprise X or Y zeolites. X or Y zeolites are typically used because they have a relatively large adsorption capacity, are commercially available on a large scale, and can be formulated to adsorb PX relatively stronger than all three other $C_8$ aromatic isomers, EB, OX, and MX as exhibited by the selectivity. To a great extent the properties desirable for a good adsorbent are a compromise and require the careful balancing of the properties of the adsorbent or the adsorbent/desorbent pair. For example the PX selectivity of X or Y zeolites relative to the other $C_8$ aromatic isomers is only satisfactory.

Prior Patents that discuss the preparation and use of some of the preferred adsorbents useful in the present invention include U.S. Pat. No. 4,826,667 (SSZ-25), U.S. Pat. No. 4,439,409, and U.S. Pat. No. 4,954,325. The '667 patent to Zones et al. discusses preparation of SSZ-25 using an adamantane based template. The '667 patent also discloses on column 13 line 6 that "SSZ-25 can also be used as an adsorbent. . . ." However, the '667 does not provide any elaboration or disclosure as to the use of SSZ-25 as an adsorbent.

An adsorbent having improved PX selectivity relative to the other $C_8$ aromatic isomers can have substantial economic advantages over prior art processes The process of the present invention provides just such advantages.

SUMMARY OF THE INVENTION

The present invention relates to an adsorptive process for the separation and purification of paraxylene from a hydrocarbon feed comprising a mixture of $C_8$ aromatic hydrocarbons comprising:
  a) contacting the feed, at adsorption conditions with an adsorbent bed comprising an adsorbent selected from the group consisting of SSZ-25, MCM-22, PSH-3, ERB-1, and ITQ-1 thereby adsorbing paraxylene from the feed;
  b) contacting the adsorbent bed at desorption conditions with a desorbent material comprising benzene;
  c) withdrawing a stream comprising desorbent and less selectively adsorbed components of the feed from the adsorbent bed;
  d) withdrawing from the adsorbent bed a stream comprising desorbent and said paraxylene;
  e) separating the stream comprising desorbent and less selectively adsorbed components into a second stream comprising desorbent and a stream comprising less selectively adsorbed components;
  f) separating the stream comprising desorbent and said paraxylene into a third stream comprising desorbent and a stream comprising paraxylene.

An alternative embodiment of the present invention employs a two stage process for the production of paraxylene from a feed comprising $C_8$ aromatic isomers, comprising:
  an adsorption step, using an adsorbent selected from the group consisting of SSZ-25, MCM-22, PSH-3, ERB-1, and ITQ-1 to form a stream concentrated in paraxylene from the feed comprising $C_8$ aromatic isomers; and
  a crystallization step to purify the stream concentrated in paraxylene to obtain high purity paraxylene product suitable for use in the production of terephthalic acid or dimethylterephthalate.

Another embodiment of the present invention comprises a process for the production of high purity paraxylene from a feed comprising paraxylene and at least one other $C_8$ aromatic hydrocarbon, comprising:

a) adsorption of the paraxylene from the feed on an adsorbent selected from the group consisting of SSZ-25, MCM-22, PSH-3, ERB-1, and ITQ-1 at adsorption conditions;

b) desorption of the paraxylene from the adsorbent using a desorbent to form a stream comprising desorbent and paraxylene; and c) separation of the stream comprising desorbent and paraxylene to form a stream comprising paraxylene and a stream comprising desorbent Among other factors the present invention is based on the finding that an adsorbent comprising SSZ-25 zeolite or its isostructural equivalents MCM-22, PSH-3, ERB- 1, and ITQ- 1 is particularly useful in an adsorption process for the separation and purification of paraxylene from a feed comprising xylenes and ethylbenzene. In a particularly preferred embodiment the zeolite adsorbent has at least a portion of exchangeable cationic sites exchanged with Cesium. In another particularly preferred embodiment of the present invention, the desorbent used in the present invention comprises benzene. Use of benzene desorbent results in a much greater boiling point difference between xylenes and benzene than between xylenes and conventionally used desorbents such as toluene and para-diethylbenzene. This large boiling point difference leads to easier distillation in the extract and raffinate distillation columns of the process resulting in capital and operating cost savings.

DDESCRIPTION OF THE INVENTION

The present invention provides process for the production of PX from a stream comprising $C_8$ aromatic isomers using adsorption to separate the PX from the OX, MX, and EB isomers to obtain high purity PX product suitable for use in the production of terephthalic acid or dimethylterephthalate using a zeolite molecular sieve adsorbent selected from the group consisting of SSZ-25, MCM-22, PSH-3, ERB-1,and ITQ-1. By high purity PX product we mean PX of at least 99.5 wt. % purity, preferably at least 99.7 wt. % purity, more preferably at least 99.8 wt % purity and most preferably at least 99.9 wt. % purity as determined by gas chromatographic methods. A Gas Chromatography method useful for the determination of both PX purity and specific amounts of impurities is ASTM D-3798 which is herein incorporated by reference.

The SSZ-25 zeolite component of the catalyst used in the process of the present invention can be prepared in various manners. Suitable preparation procedures are described in U.S. Pat. No. 4,826,667 to Zones et al. which is herein incorporated by reference in its entirety.

SSZ-25 zeolite embraces a family of crystalline aluminosilicates that also includes MCM-22, PSH-3, ITQ-1, and ERB-1

The structure of the SSZ-25 class of molecular sieves is such that the pore sizes or apertures of the zeolite are in the intermediate size range of approximately 4 to 7 Angstroms, usually about 5 Angstroms on average. This is in contrast to the larger pore size zeolites, such as faujasite, or the smaller pore size zeolites such Linde Type A and erionite. The structure of SSZ-25/MCM-22is described in Microporous and Mesoporous Materials 23 (1998) 109–117 Twelve-ring pockets on the external surface of MCM-22 crystals. The pore opening into the crystalline zeolite is delineated by the atomic structure. However, the pore opening or constraints may be modified by components added to the SSZ-25.

Although SSZ-25 is the preferred molecular sieve for use in the catalyst used in the process of the present invention, other zeolites of the SSZ-25 structural type are embraced within a broad embodiment of the present invention. These zeolites include MCM-22, which is described in U.S. Pat. No. 4,954,325 the disclosures of which is incorporated by reference into the present specification. PSH-3 is described in U.S. Pat. No. 4,439,409 which is also incorporated by reference in its entirety. ERB-1 is descussed in Microporous Materials 6 (1996) 395–404 Experimental and computational study of beta, ZSM-12, Y, mordenite and ERB-1 in cumene synthesis. ITQ-1 is described in J.

Am. Chem Soc. 1997, 119, 11000–11005 Use of Electron Microscopy and Microdiffraciton for Zeolite Framework Comparison.

SSZ-25 can be made in a variety of ways e.g. with and without seeding, and with various templates. One way of making SSZ-25 is exemplified below. SSZ-25 zeolites can be suitably prepared from an aqueous solution containing sources of an alkali metal oxide, an adamantane quaternary ammonium ion, an oxide of aluminum, gallium, iron, boron or mixtures thereof, and an oxide of silicon or germanium, or mixture of the two. The reaction mixture should have a composition in terms of mole ratios falling within the following ranges:

| | Broad | Preferred |
|---|---|---|
| $YO_2/W_2O_3$ | 20–200 | 30–100 |
| $OH^-/YO_2$ | 0.10–1.0 | 0.20–0.40 |
| $Q/YO_2$ | 0.15–0.50 | 0.15–0.30 |
| $M^+/YO_2$ | 0.05–0.30 | 0.15–0.30 |
| $H_2O/YO_2$ | 20–300 | 35–60 |
| $Q/Q + M^+$ | 0.30–0.70 | 0.40–0.67 | wherein Q is an adamantane quaternary ammonium ion, Y is silicon, germanium or both, and W is aluminum, gallium, iron, boron or mixtures thereof. M is an alkali metal, preferably sodium or potassium. The organic adamantane compound which acts as a source of the adamantane quaternary ammonium ion employed can provide hydroxide ion.

When using the adamantane quaternary ammonium hydroxide compound as a template, it has also been found that purer forms of SSZ-25 are prepared when there is an excess of the adamantane quaternary ammonium hydroxide compound present relative to the amount of alkali metal hydroxide and that when the $OH^-/SiO_2$ molar ratio is greater than 0.40, then $M^+/SiO_2$ molar ratio should be less than 0.20.

The adamantane quaternary ammonium ion component Q, of the crystallization mixture, is derived from an adamantane quaternary ammonium compound. Preferably, the adamantane quaternary ammonium ion is derived from a compound of the formula

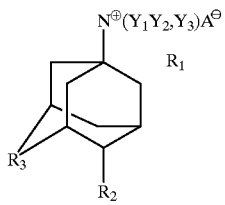

wherein each of $Y_1$, $Y_2$, and $Y_3$ independently is lower alkyl and most preferably methyl; $A^-$ is an anion which is not detrimental to the formation of the zeolite; and each of $R_1$, $R_2$, and $R_3$ independently is hydrogen, or lower alkyl and most preferably hydrogen; and

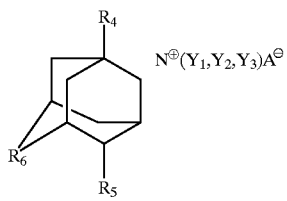

wherein each of $R_4$, $R_5$ and $R_6$ independently is hydrogen or lower alkyl; and most preferably hydrogen; each of $Y_1$, $Y_2$, and $Y_3$ independently is lower alkyl and most preferably methyl; and $A^-$ is an anion which is not detrimental to the formation of the zeolite.

The adamantane quaternary ammonium compounds are prepared by methods known in the art.

By lower alkyl is meant alkyl of from about 1 to 5 carbon atoms.

$A^-$ is an anion which is not detrimental to the formation of the zeolite. Representative of the anions include halide, e.g., fluoride, chloride, bromide and iodide, hydroxide, acetate, sulfate, carboxylate, etc. Hydroxide is the most preferred anion. It may be beneficial to ion-exchange, for example, the halide for hydroxide ion, thereby reducing or eliminating the alkali metal hydroxide quantity required.

The reaction mixture is prepared using standard zeolitic preparation techniques. Typical sources of aluminum oxide for the reaction mixture include aluminates, alumina, and aluminum compounds such as $AlCl_3$ and $Al_2(SO_4)_3$. Typical sources of silicon oxide include silicates, silica hydrogel, silicic acid, colloidal silica, tetraalkyl orthosilicates, and silica hydroxides. Gallium, iron, boron and germanium can be added in forms corresponding to their aluminum and silicon counterparts. Salts, particularly alkali metal halides such as sodium chloride, can be added to or formed in the reaction mixture. They are disclosed in the literature as aiding the crystallization of zeolites while preventing silica occlusion in the lattice.

The reaction mixture is maintained at an elevated temperature until the crystals of the zeolite are formed. The temperatures during the hydrothermal crystallization step are typically maintained from about 140. degree. C. to about 200. degree. C., preferably from about 160. degree. C. to about 180. degree. C. and most preferably from about 170. degree. C. to about 180. degree. C. The crystallization period is typically greater than 1 day and preferably from about 5 days to about 10 days.

The hydrothermal crystallization is conducted under pressure and usually in an autoclave so that the reaction mixture is subject to autogenous pressure. The reaction mixture can be stirred during crystallization.

Once the zeolite crystals have formed, the solid product is separated from the reaction mixture by standard mechanical separation techniques such as filtration. The crystals are water-washed and then dried, e.g., at 90. degree. C. to 150. degree. C. for from 8 to 24 hours, to obtain the as synthesized, SSZ-25 zeolite crystals. The drying step can be performed at atmospheric or subatmospheric pressures.

During the hydrothermal crystallization step, the SSZ-25 crystals can be allowed to nucleate spontaneously from the reaction mixture. The reaction mixture can also be seeded with SSZ-25 crystals both to direct, and accelerate the crystallization, as well as to minimize the formation of undesired aluminosilicate contaminants. If the reaction mixture is seeded with SSZ-25 crystals, the concentration of the organic compound can be greatly reduced or eliminated, but it is preferred to have some organic compound present, e.g., an alcohol.

The synthetic SSZ-25 zeolites can be used as synthesized or can be thermally treated (calcined). Usually, it is desirable to remove the alkali metal cation by ion exchange and replace it with hydrogen, ammonium, or any desired metal ion. The zeolite can be leached with chelating agents, e.g., EDTA or dilute acid solutions, to increase the silica:alumina mole ratio. The zeolite can also be steamed; steaming helps stabilize the crystalline lattice to attack from acids. Typical replacing cations can include metal cations, e.g., rare earth, Group IIA and Group VIII metals, as well as their mixtures. Of the replacing metallic cations, cations of metals such as rare earths, Mn, Ca, Mg, Zn, Cd, Pt, Pd, Ni, Co, Ti, Al, Sn, Fe and Co are preferred. For the adsorbent useful in the process of the present invention $C_8$ (Cesiun) is preferred as a replacing cation.

In a more preferred embodiment of the present invention a majority of the replaceable cations are replaced with Cesium.

The hydrogen, ammonium, and metal components can be exchanged into the zeolite. The zeolite can also be impregnated with the metals, or, the metals can be physically intimately admixed with the zeolite using standard methods known to the art. And, the metals can be occluded in the crystal lattice by having the desired metals present as ions in the reaction mixture from which the SSZ-25 zeolite is prepared.

Typical ion exchange techniques involve contacting the synthetic zeolite with a solution containing a salt of the desired replacing cation or cations. Although a wide variety of salts can be employed, chlorides and other halides, nitrates, and sulfates are particularly preferred. Representative ion exchange techniques are disclosed in a wide variety of patents including U.S. Pat. Nos. 3,140,249; 3,140,251; and 3,140,253 which are incorporated herein by reference. Ion exchange can take place either before or after the zeolite is calcined.

Following contact with the salt solution of the desired replacing cation, the zeolite is typically washed with water and dried at temperatures ranging from 65. degree. C. to about 315. degree. C. After washing, the zeolite can be calcined in air or inert gas at temperatures ranging from about 200. degree. C. to 820. degree. C. for periods of time ranging from 1 to 48 hours, or more, to produce a catalytically active product especially useful in hydrocarbon conversion processes.

Regardless of the cations present in the synthesized form of the zeolite, the spatial arrangement of the atoms which form the basic crystal lattice of the zeolite remains essentially unchanged. The exchange of cations has little, if any, effect on the zeolite lattice structures.

The SSZ-25 aluminosilicate can be formed into a wide variety of physical shapes. Generally speaking, the zeolite can be in the form of a powder, a granule, or a molded product, such as extrudate having particle size sufficient to pass through a 2-mesh (Tyler) screen and be retained on a 400-mesh (Tyler) screen. In cases where the catalyst is molded, such as by extrusion with an organic binder, the aluminosilicate can be extruded before drying, or, dried or partially dried and then extruded. The zeolite can be composited with other materials resistant to the temperatures and other conditions employed in organic conversion processes. Such matrix materials include active and inactive materials and synthetic or naturally occurring zeolites as well as inorganic materials such as clays, silica and metal oxides. The latter may occur naturally or may be in the form of gelatinous precipitates, sols, or gels, including mixtures of silica and metal oxides. Use of an active material in conjunction with the synthetic zeolite, i.e., combined with it, tends to improve the conversion and selectivity of the catalyst in certain organic conversion processes. Inactive materials can suitably serve as diluents to control the amount of conversion in a given process so that products can be obtained economically without using other means for controlling the rate of reaction. Frequently, zeolite materials have been incorporated into naturally occurring clays, e.g., bentonite and kaolin. These materials, i.e., clays, oxides, etc., function, in part, as binders for the catalyst. It is desirable to provide a catalyst having good crush strength, because in petroleum refining the catalyst is often subjected to rough handling. This tends to break the catalyst down into powders which cause problems in processing.

Naturally occurring clays which can be composited with the synthetic zeolites of this invention include the montmorillonite and kaolin families, which families include the sub-bentonites and the kaolins commonly known as Dixie, McNamee, Georgia and Florida clays or others in which the main mineral constituent is halloysite, kaolinite, dickite, nacrite, or anauxite. Fibrous clays such as sepiolite and attapulgite can also be used as supports. Such clays can be used in the raw state as originally mined or can be initially subjected to calcination, acid treatment or chemical modification.

In addition to the foregoing materials, the SSZ-25 zeolites can be composited with porous matrix materials and mixtures of matrix materials such as silica, alumina, titania, magnesia, silica: alumina, silica-magnesia, silica-zirconia, silica-thoria, silica-beryllia, silica-titania, titania-zirconia as well as ternary compositions such as silica-alumina-thoria, silica-alumina-zirconia, silica-alumina-magnesia and silica-magnesia-zirconia. The matrix can be in the form of a cogel.

The SSZ-25 zeolites can also be composited with other zeolites such as synthetic and natural faujasites (e.g., X and Y), erionites, and mordenites. They can also be composited with purely synthetic zeolites such as those of the ZSM series. The combination of zeolites can also be composited in a porous inorganic matrix.

After calcination the SSZ-25 zeolites have a crystalline structure whose X-ray powder diffraction pattern shows the following characteristic lines as indicated in Table 2 below:

TABLE 2

| 2θ | d/n | I/I$_o$ |
|---|---|---|
| 3.4 | 25.5 | 17 |
| 7.19 | 12.30 | 100 |
| 8.04 | 11.00 | 55 |
| 10.06 | 8.78 | 63 |
| 14.35 | 6.17 | 40 |
| 16.06 | 5.51 | 17 |
| 22.77 | 3.90 | 38 |
| 23.80 | 3.74 | 20 |
| 26.08 | 3.417 | 65 |

In the process of the present invention, it is preferred to use the zeolite in a "bound" form, that is, with a refractory oxide as a binder for the overall catalyst particle. Suitable refractory oxide binders are alumina, silica, titania, clay, or mixtures thereof This binder serves to hold the crystalline zeolite particles together in a catalyst particle of suitable size and suitable attrition resistance upon handling and use in the adsorption process. The amount of binder used versus zeolite is preferably between 5 and 50 percent binder by weight, more preferably between 10 and 40 percent binder.

For simulated moving bed separation, the selectivity of the PX vs. the esorbent is an extremely important parameter. The selectivity, as used throughout this specification, is defined as the ratio of the two components of the absorbed or retained phase over the ratio of the same two components in the unadsorbed phase at equilibrium conditions. Selectivity is derived as follows:

$$\text{Selectvity} = S_{A,B} = \frac{(A \text{ adsorbed on zeolite})}{(B \text{ adsorbed on zeolite})} \times \frac{(B \text{ in solution})}{(A \text{ in solution})}$$

where A and B are the two components of the feed represented in volume percentages.

A selectivity of greater than 1 means that the PX is more strongly adsorbed than the desorbent. A selectivity of less than 1 means that the PX is less strongly adsorbed than the desorbent. It is preferable that the desorbent be about as strongly adsorbed as the C$_8$ aromatic isomers. Most preferably the desorbent is adsorbed less strongly than the desired PX isomer but more strongly than the next most strongly adsorbed C$_8$ aromatic isomer. If the desorbent is adsorbed too strongly, an excessive fraction of the total capacity of the adsorbent is occupied by the desorbent. This effectively reduces the portion of the adsorbent that is available to adsorb and separate the C$_8$ aromatic isomers, and increases the amount of adsorbent that must be used. If the desorbent is not adsorbed strongly enough, large amounts of desorbent must be used, causing a high desorbent to feed ratio and increasing the capital and operating costs of the process.

To separate the paraxylene from a feed mixture containing paraxylene and at least one other C$_8$ aromatic, the mixture is contacted with the adsorbent at adsorption conditions and the paraxylene is more selectively adsorbed and retained by the adsorbent while the other components are less selectively adsorbed and are partially removed from the interstitial void spaces between the particles of adsorbent and from the surface of the adsorbent. The adsorbent containing the more selectively adsorbed paraxylene is referred to as a "rich" adsorbent—rich in the more selectively adsorbed paraxylene. The paraxylene is then recovered from the rich adsorbent by contacting the rich adsorbent with a desorbent material at desorption conditions. According to one embodiment of the present invention, this partially purified paraxylene is then subjected to crystallization at crystallization conditions to produce high purity paraxylene.

The adsorptive separation portion of this process is generally operated continuously at substantially constant pressures and temperatures to ensure liquid phase, and the desorbent material relied upon must be judiciously selected to satisfy several criteria. First, the desorbent material should displace an extract component from the adsorbent with reasonable mass flow rates without itself being so strongly adsorbed as to unduly prevent the extract component from displacing the desorbent material in a following adsorption cycle. Secondly, the desorbent material must be compatible with the particular adsorbent and the particular feed mixture. More specifically, it must not reduce or destroy the critical selectivity of the adsorbent for an extract component with respect to the raffinate component or react chemically with the feed components. Desorbent materials should additionally be easily separable from the feed mixture that is passed into the process. Both the raffinate components and the extract components are typically removed from the adsorbent in admixture with desorbent material and without a method of separating at least a portion of desorbent material, the purity of the extract product and the raffinate product would not be very high nor would the desorbent material be available for reuse in the process. It is, therefore, contemplated that any desorbent material used in this process will have a substantially different average boiling point than that of the feed mixture or any of its components, i.e., more than about 20° centigrade difference, to allow separation of at least a portion of the desorbent material from feed components in the extract and raffinate streams by simple fractional distillation, thereby permitting reuse of desorbent material in the process. Finally, desorbent materials should be readily available and reasonable in cost.

As discussed above there are several criteria that an adsorbent/desorbent pair must meet. A suitable desorbent or desorbents for a particular separation with specific adsorbent are generally not predictable.

Crystallization has in general been found to be a very efficient and effective method for the final purification of paraxylene to form high purity paraxylene in an alternate embodiment of the process of the present invention. Regarding the crystallization step that can be used in an alternative embodiment of the process of the present invention a number of variations are possible. In one variation, the stream comprising paraxylene can be crystallized in a crystallization zone to produce a suspension of paraxylene crystals in the mother liquor, the crystals are separated from the mother liquor in a separation zone, the crystals can be washed with a suitable wash solvent, the mother liquor can be recovered and sent to the adsorption zone and very high purity paraxylene crystals are recovered. The wash liquor is recovered and recycled to a distillation zone if the wash solvent contains toluene or to the crystallization zone or the adsorption zone if the wash solvent is molten paraxylene.

In a second variation which may be preferred with certain types of crystallizer, for example scraped surface crystallizers, the xylenes are crystallized in at least two crystallization zones, one of which is at a colder temperature than the other, the mother liquor from the coldest crystallization zone being recovered and sent to the adsorption zone.

Whatever the variation, the paraxylene is preferably crystallized at high temperature, for example between +10° C. and −34° C. and in particular between +10° C. and −25° C. More precisely, the lower temperature zone is at a temperature in the range 0° C. to −25° C. for example, while the higher temperature zone is at a temperature which is in the range +10° C. to −5° C., for example.

In the second variation discussed above, the stream comprising paraxylene is crystallized in a first high temperature crystallization zone, first paraxylene crystals are separated from a first mother liquor, the first mother liquor is recrystallized in a second lower temperature crystallization zone. Second paraxylene crystals are separated from a second mother liquor which is sent to the adsorption zone, the first and second crystals are washed with a suitable wash solvent, melted, and very high purity paraxylene is recovered, and at least a portion of the wash liquor is recycled to the first crystallization zone or to the second crystallization zone and/or to the adsorption zone.

In a further implementation of the process, after having been crystallized and separated from its mother liquor, the paraxylene can be taken up again into suspension in a partial melting/resuspension zone as described in U.S. patent application Ser. No. 08/875,278 (French patent application FR 95/00746) which is hereby incorporated by reference in its entirety. Other references that disclose paraxylene crystallization technology that is suitable for use in the process of the present invention are U.S. Pat. No. 5,811,629 as well as copending patent applications U.S. Ser. No. 08/860,558 and U.S. Ser. No. 08/860,559 all of which are herein incorporated by reference in their entirety.

In more detail, in a first variation the stream comprising paraxylene is crystallized in a crystallization zone to produce a suspension of paraxylene crystals in a mother liquor, the crystals are separated from the mother liquor and then reslurried in a partial melting/resuspension zone. A second suspension of crystals is recovered. The second suspension (resuspension) is separated and washed in a separation and washing zone using a wash solvent which can be toluene or molten, very high purity paraxylene. Very high purity paraxylene is recovered which is optionally melted, and a wash liquor is recovered which is at least partially recycled to the crystallization zone and/or to the adsorption zone after optional distillation if the wash solvent is toluene.

In a second variation, the stream comprising paraxylene from the adsorption step is crystallized in a first high temperature crystallization zone, first crystals of paraxylene are separated from a first mother liquor, the first mother liquor is recrystallized in a second lower temperature crystallization zone. Second paraxylene crystals are separated from a second mother liquor which is preferably sent to the adsorption zone. The first and second-crystals are washed with a wash solvent which is toluene or molten very high purity paraxylene. The first and second crystals are resuspended and optionally partially melted in at least one partial melting/resuspension zone. The resuspension is separated and washed in a separation and washing zone (such as a centrifuge, filter, or wash column) with a wash solvent which can be toluene or molten very high purity paraxylene. Very high purity paraxylene is recovered and optionally melted. A wash liquor is recovered, and at least a portion of the wash liquor can be recycled to the first and/or second crystallization zone, and/or to the adsorption zone.

The remaining portion of the wash liquor which is not recycled to the crystallization or adsorption zone can be introduced to the partial melting/resuspension zone where the crystals obtained, which are smaller in size, are taken up into suspension.

The mother liquor from the crystallization can be optionally recycled to be selectively adsorbed in the adsoption section of the present invention, preferably a simulated moving bed containing at least 3 zones. It may be a simulated counter-current moving bed (U.S. Pat. No. 2,985, 989) or a simulated co-current bed (U.S. Pat. No. 4,498,991 and U.S. Pat. No. 4,402,832), all of which are hereby incorporated by reference.

EXAMPLES

I performed the following tests in order to determine the effectiveness of SSZ-25 adsorbents and adsorbent/desorbent pairs. The comparative examples were performed in order to provide a comparison of the effectiveness of the SSZ-25 adsorbents with a commercially available and commercially successful adsorbent currently used commercially in large scale PX adsorption units (Ba X zeolite).

EXAMPLE 1

Cs SSZ-25 Adsorbent with Benzene Desorbent

Equal amounts, about 0.1 gram, of benzene and commercially available mixed xylenes (Aldrich) were added to a vial. About 0.6 g iso-octane was also added. The iso-octane served both as a non-adsorbing tracer, to allow for determination of the adsorption capacity of the adsorbent, and as a diluent, to raise the liquid level in the vial above the level of the adsorbent which was to be added. The initial composition of the liquid mixture was determined by G.C. About 0.5 gram of Cs SSZ-25 was then added to the vial. The vial was sealed and the system was allowed to come to equilibrium by heating to about 60° C. for about 4 hours. The final liquid compostion was then determined by G.C., and the adsorbent capacity and selectivities were determined.

| | |
|---|---|
| Adsorption capacity (grams adsorbed/gram adsobent) | 0.0895 |
| Selectivity, PX/EB | 2.32 |
| Selectivity, PX/MX | 10.1 |
| Selectivity, PX/OX | 6.83 |
| Selectivity, PX/benzene | 1.04 |

The example shows that $C_8$ SSZ-25 with a benzene desorbent is effective for separating PX from a $C_8$ aromatic mixture. PX is adsorbed more strongly than the other $C_8$ aromatic isomers, and the benzene desorbent is adsorbed about as strongly as paraxylene.

Comparative Example 1

Ba exchanged X zeolite with Toluene Desorbent

As in Example 1, equal amounts of mixed xylenes and desorbent were added to a vial, along with an inert diluent. The liquid composition was determined by G.C., the adsorbent was added, the system was allowing to reach equilibrium, the final liquid composition was measured by G.C., and the adsorbent capacity and selectivities were determined.

| | |
|---|---|
| Adsorption capacity (grams adsorbed/gram adsobent) | 0.146 |
| Selectivity, PX/EB | 1.71 |
| Selectivity, PX/MX | 3.09 |
| Selectivity, PX/OX | 2.01 |
| Selectivity, PX/toluene | 1.36 |

The example shows that Ba X zeolite with a toluene desorbent is effective for separating PX from a $C_8$ aromatic mixture. PX is adsorbed more strongly than the other $C_8$ aromatic isomers, and the toluene desorbent is adsorbed about as strongly as paraxylene. Compared to the Cs SSZ-25 adsorbent, the Ba X adsorbent has a greater adsorption capacity but lower selectivities for PX versus the other $C_8$ aromatic isomers.

However, the Cs SSZ-25/benzene adsorbent/desorbent system has a particular advantage in that the benzene is a significantly lower boiling desorbent than is the toluene in the Ba X/toluene adsorbent/desorbent system. Separation of a benzene desorbent from xylenes in adsorber extract and raffinate streams is easier than is separation of a toluene desorbent from xylenes in those streams.

The use of a Cs SSZ-25 adsorbent with a benzene desorbent for the separation of PX from a $C_8$ aromatics stream would allow for significant capital and operating cost saving in the distillation section immediately downstream from the adsorber.

Comparative Example 2

Ba exchanged X zeolite with Benzene Desorbent

As in Example 1, equal amounts of mixed xylencs and desorbent were added to a vial, along with an inert diluent. The liquid composition was determined by G.C., the adsorbent was added, the system was allowing to reach equilibrium, the final liquid composition was measured by G.C., and the adsorbent capacity and selectivities were determined.

| | |
|---|---|
| Adsorption capacity (grams adsorbed/gram adsobent) | 0.160 |
| Selectivity, PX/EB | 0.67 |
| Selectivity, PX/MX | 1.18 |
| Selectivity, PX/OX | 0.93 |
| Selectivity, PX/benzene | 0.52 |

The example shows that Ba X zeolite with a benzene desorbent is not effective for separating PX from a $C_8$ aromatic mixture. PX is not adsorbed more strongly than the other $C_8$ aromatic isomers, and the benzene desorbent is adsorbed more strongly as paraxylene.

Ba X zeolite cannot be used with a low-boiling, benzene desorbent to separate PX from a $C_8$ aromatic mixture.

Comparative Example 3

Cs SSZ-25 with Toluene Desorbent

As in Example 1, equal amounts of mixed xylenes and desorbent were added to a vial, along with an inert diluent. The liquid composition was determined by G.C., the adsorbent was added, the system was allowing to reach equilibrium, the final liquid composition was measured by G.C., and the adsorbent capacity and selectivities were determined.

| | |
|---|---|
| Adsorption capacity (grams adsorbed/gram adsobent) | 0.105 |
| Selectivity, PX/EB | 1.66 |
| Selectivity, PX/MX | 7.41 |
| Selectivity, PX/OX | 4.38 |
| Selectivity, PX/toluene | 0.67 |

The example shows that Cs SSZ-25 zeolite with a toluene desorbent is not as effective for separating PX from a C8 aromatic mixture as is Cs SSZ-25 with a benzene desorbent.

The major disadvantage is that the toluene desorbent is adsorbed significantly more strongly than the paraxylene.

What is claimed is:

1. A process for the separation and purification of paraxylene from a hydrocarbon feed comprising a mixture of $C_8$ aromatic hydrocarbons, comprising:
   a) contacting the feed, at adsorption conditions, with an adsorbent bed comprising an adsorbent selected from the group consisting of SSZ-25, MCM-22, PSH-3, ERB-1, and ITQ-1 thereby adsorbing paraxylene from the feed;
   b) contacting the adsorbent bed at desorption conditions with a desorbent material comprising benzene;
   c) withdrawing a stream comprising desorbent and less selectively adsorbed components of the feed from the adsorbent bed; and
   d) withdrawing from the adsorbent bed a stream comprising desorbent and said paraxylene,
   e) separating the stream comprising desorbent and less selectively adsorbed components into a stream comprising desorbent and a stream comprising less selectively adsorbed components; and
   f) separating the stream comprising desorbent and said paraxylene into a stream comprising desorbent and a stream comprising paraxylene.

2. A two stage process for the production of paraxylene from a feed comprising $C_8$ aromatic isomers, comprising:
   a) an adsorption step, using an adsorbent selected from the group consisting of SSZ-25, MCM-22, PSH-3, ERB-1, and ITQ-1 to form a stream concentrated in paraxylene from the feed comprising $C_8$ aromatic isomers; and
   b) a crystallization step to purify the stream concentrated in paraxylene to obtain high purity paraxylene product suitable for use in the production of terephthalic acid or dimethylterephthalate.

3. A process for the production of high purity paraxylene from a feed comprising paraxylene and at least one other $C_8$ aromatic hydrocarbon, comprising:
   a) adsorption of the paraxylene from the feed on an adsorbent selected from the group consisting of SSZ-25, MCM-22, PSH-3, ERB-1, and ITQ-1 at adsorption conditions;
   b) desorption of the paraxylene from the adsorbent using a desorbent to form a stream comprising desorbent and paraxylene; and
   c) separation of the stream comprising desorbent and paraxylene to form a stream comprising paraxylene and a stream comprising desorbent.

4. The process of claim 1 wherein the adsorbent further comprises Cesium ions exchanged at exchangeable cationic sites.

5. The process of claim 2 wherein the adsorption step is a simulated moving bed counter-current adsorption process.

6. The process of claim 2 wherein the adsorbent further comprises Cesium ions exchanged at exchangeable cationic sites.

7. The process of claim 3 wherein the adsorbent further comprises Cesium ions exchanged at exchangeable cationic sites.

8. The process of claims 2 wherein the high purity paraxylene is at least 99.5 wt. % paraxylene purity.

9. The process of claim 2 wherein the high purity paraxylene is at least 99.7 wt. % paraxylene purity.

10. The process of claim 2 wherein the high purity paraxylene is at least 99.8 wt. % paraxylene purity.

11. The process of claim 1 wherein the stream comprising paraxylene has a paraxylene purity of at least 99.7 wt %.

12. The process of claim 3 wherein the stream comprising paraxylene has a paraxylene purity of at least 99.7 wt. %.

13. The process of claim 2 wherein the stream concentrated in paraxylene has a paraxylene concentration of between about 80% and 98%.

14. The process of claim 2 wherein the stream concentrated in paraxylene has a paraxylene concentration of between about 85% and 95%.

15. The process of claim 1 wherein the adsorbent further comprises Cesium ions exchanged at a majority of exchangeable cationic sites.

16. The process of claim 2 wherein the adsorbent further comprises Cesium ions exchanged at a majority of exchangeable cationic sites.

17. The process of claim 3 wherein the adsorbent further comprises Cesium ions exchanged at a majority of exchangeable cationic sites.

* * * * *